United States Patent [19]
Carpenter et al.

[11] 3,956,244
[45] May 11, 1976

[54] CROSSLINKED VINYL ACETATE-MALEIC ANHYDRIDE HETEROPOLYMERS AND DERIVATIVES PREPARED FROM THEM

[75] Inventors: William G. Carpenter, Cranbury; Daniel F. Herman, Princeton; Rudolph J. Berndlmaier, Allentown, all of N.J.

[73] Assignee: N L Industries, Inc., New York, N.Y.

[22] Filed: Dec. 24, 1974

[21] Appl. No.: 536,224

Related U.S. Application Data

[63] Continuation-in-part of Ser. No. 409,791, Oct. 26, 1973, abandoned.

[52] U.S. Cl.................................. 526/79; 424/49; 424/78; 526/219; 526/272; 526/230; 526/227; 526/231; 526/232; 526/324; 526/330; 526/326
[51] Int. Cl.². ................. C08F 2/06; C08F 218/08
[58] Field of Search .............. 260/78.5 R, 78.5 T

[56] References Cited
UNITED STATES PATENTS

| 2,971,939 | 2/1961 | Baer | 260/45.5 |
|---|---|---|---|
| 3,085,986 | 4/1963 | Muskat | 260/31.8 |
| 3,165,486 | 1/1965 | Johnson | 260/29.7 |
| 3,398,092 | 8/1968 | Fields et al. | 210/24 |
| 3,415,745 | 12/1968 | Isaacson et al. | 210/54 |
| 3,554,985 | 1/1971 | Fields et al. | 260/78.5 |
| 3,557,067 | 1/1971 | Burns et al. | 260/78.5 |
| 3,660,339 | 5/1972 | Schuh | 260/29.7 D |

Primary Examiner—John Kight, III

[57] ABSTRACT

Novel crosslinked heteropolymers of vinyl acetate and maleic anhydride are provided which are useful as aqueous thickeners for aqueous formulations such as cosmetics and latex paints. Ester and amide derivatives of the combined maleic anhydride portion of the heteropolymer are also provided. The process for preparing the crosslinked heteropolymers comprises adding a maleic anhydride monomer, and crosslinking agent monomer, and catalyst in controlled amounts to a monomer solution of vinyl acetate.

11 Claims, No Drawings

CROSSLINKED VINYL ACETATE-MALEIC ANHYDRIDE HETEROPOLYMERS AND DERIVATIVES PREPARED FROM THEM

This application is a Continuation-In-Part of parent application, Ser. No. 409,791, filed 10/26/73, now abandoned.

BACKGROUND OF THE INVENTION

This invention is concerned with a novel process for preparing crosslinked vinyl ester-maleic derivative heteropolymers and derivatives thereof, particularly crosslinked vinyl acetate-maleic anhydried heteropolymers for use as gellants, thickeners and additives for aqueous formulations. In addition, this invention is also concerned with crosslinked heteropolymers prepared by this process.

In the past, crosslinked co-polymers of vinyl esters such as vinyl acetate, and maleic derivatives, such as maleic anhydride, maleic acid, maleic acid esters and maleic acid salts have been described which contain molar ratios of combined vinyl ester to maleic derivative of 1:1 to about 10:1. These polymers have found limited utility in a variety of applications including soil-treatment additives, drilling fluid additives, adhesives and dispersion aids. Generally, these copolymers have been produced by conventional polymerization techniques such as mass, solution, or emulsion polymerization. When aqueous solutions are prepared utilizing copolymers of these conventional processes, the solutions are generally cloudy and exhibit low viscosities and poor viscosity stabilities.

The instant invention is primarily concerned with novel crosslinked maleic anhydride-vinyl acetate heteropolymers which are excellent gellants for aqueous systems and with novel processes for preparing them. In contrast to the prior art these novel crosslinked heteropolymers when incorporated into aqueous systems impart high viscosity with excellent viscosity stability. In addition, many form clear gels which are highly desirable in formulations such as cosmetics.

SUMMARY OF THE INVENTION

It is an object of this invention to provide crosslinked heteropolymers of vinyl acetate and maleic anhydride having aqueous gelling properties.

It is an object of this invention to provide derivatives of said crosslinked heteropolymers.

It is a further object of this invention to provide crosslinked heteropolymers of vinyl ester and maleic derivatives imparting high viscosities to aqueous systems.

It is still a further object of this invention to provide crosslinked heteropolymers of vinyl ester and maleic derivatives which maintain high degrees of clarity in aqueous systems.

It is an even still further object of this invention to provide aqueous formulations containing crosslinked heteropolymers of maleic anhydride and vinyl acetate as gellants therefor.

This invention pertains to crosslinked heteropolymers of combined vinyl ester and maleic derivatives. The mole ratio of the combined vinyl ester to the combined maleic derivative is from 1.1:1 to 3:1.

In particular this invention is concerned with crosslinked heteropolymers of vinyl acetate and maleic anhydride.

These crosslinked heteropolymers are produced by combining vinyl ester monomer, maleic derivative monomer, and crosslinking agent monomer wherein the mole ratio of the vinyl ester monomer to the maleic derivative monomer is from 1.1:1 to 3:1 and wherein the amount of crosslinking agent monomer is from 0.2 to 3 weight percent based on the total amount of monomer in the manner described below. A vinyl ester monomer solution, a maleic derivative monomer-crosslinking agent monomer solution, and a catalyst solution are provided. An amount of the maleic derivative-crosslinking agent monomer solution is added to the vinyl ester monomer solution to form a polymerizable solution. The addition is in an amount such that the unreacted amounts of crosslinking agent and maleic derivative monomers in the polymerizable solution do not exceed 1/15th of the total mounts to be added. An amount of the catalyst solution is also added to the polymerizable solution in an amount sufficient to promote heteropolymerization but in an insufficient amount to promote homopolymerization of the vinyl ester. The solution is then polymerized at sufficient temperature to form the crosslinked heteropolymer. The additions of crosslinking agent, maleic derivative and catalyst and the polymerization are continued until all the maleic derivative monomers, crosslinking agent monomers, and catalyst has been added and the crosslinked heteropolymer is formed wherein the mole ratio of the combined vinyl ester to combined maleic derivatives is from 1.1:1 to 3:1.

DETAIL DESCRIPTION OF THE INVENTION

The product of the instant invention is a crosslinked heteropolymer of vinyl ester and maleic derivative. The mole ratio of combined vinyl ester to combined maleic derivative is from 1.1:1 to 3:1 and preferably from 1.2:1 to 2.5:1. It is well known in the art that vinyl esters and maleic derivatives generally polymerize to form alternating copolymers since maleic derivatives such as maleic anhydride will not polymerize with itself under normal free-radical polymerization conditions. As the molar ratio of combined vinyl ester to maleic derivative is increased, a random heteropolymer is formed comprising units of alternating copolymer and units of polyvinyl acetate of varying chain lengths.

This invention is primarily concerned with vinyl ester and maleic derivative crosslinked heteropolymers wherein the vinyl ester is vinyl acetate and the maleic derivative is maleic anhydride. Other vinyl esters which can be applied in this invention are vinyl propionate, vinyl butyrate, vinyl valerate and the like, and other maleic derivatives are maleic acid, maleic acid salts, maleic acid esters and the like.

The term crosslinked is meant to describe a heteropolymer prepared in the presence of a small amount of crosslinking agent. The crosslinking agent is a polymerizable unsaturated monomer which contains more than one site of unsaturation such as dienes, trienes etc. or compounds containing both double and triple bonds. Crosslinking is achieved by addition at points of unsaturation of the crosslinking agent to the heteropolymer chain. The term crosslinked as used in the specification and appended claims is primarily meant to mean branching, that is, linear polymer segments are interconnected by the crosslinking agent to yield a polymer of finite molecular weight and polymer crosslinking is not carried out to the point of infinite molecular weight where insoluble polymers are formed which are no longer swellable in water.

The crosslinking agents employed in this invention include allyl and vinyl esters of unsaturated carboxylic acids such as allyl acrylate, allyl methacrylate, diallyl phthalate, diallyl maleate and ethylene dimethacrylate; allyl esters of inorganic acids such as triallyl phosphate; allyl heterocyclic compounds such as triallyl isocyanurate and triallyl cyanurate; unsaturated acid esters of polyols such as trimethylol propane trimethacrylate and gylcerol trimethacrylate; and olefinically unsaturated derivatives of aromatic compounds such as divinyl benzene.

The preferred crosslinking agent is allyl methacrylate. The invention, however, is not limited to the above mentioned crosslinking agents and other similar agents well known to those skilled in the art for crosslinking organic polymers may also be utilized.

The amount of crosslinking agent employed is from 0.2 to 3.0 weight percent based on the total amount of monomers and preferably from 0.5 to 2.0 weight percent.

In order to prepare the heteropolymers of the instant invention a vinyl ester monomer solution is formed by dissolving the vinyl ester monomer in a solvent. This solution becomes the reaction medium in the process. The solvent should be inert to the monomers and crosslinking agent and should be a non-solvent for formed crosslinked heteropolymers in order to aid its recovery from the mixture. Suitable solvents are the aromatic hydrocarbon solvents such as benzene, toluene and xylene. It has been found that when toluene as a solvent is employed a crosslinked heteropolymer is formed which produces aqueous gel of very high clarity.

A solution of maleic derivative monomer and crosslinking agent is also prepared utilizing a similar solvent as that employed in the vinyl ester monomer solution. The mole ratio of vinyl ester monomer in solution to the maleic derivative monomer in solution can vary from 3:1 to 1.1:1 or more. The amount of crosslinking agent can vary from 0.2 to 3.0 weight percent based on the total amount of monomers employed.

A catalyst is additionally used in the process. To determine the amount of catalyst to be employed some preliminary test, as known to the art are recommended taking into consideration the half-life of the catalyst, the amount of monomers and the temperature at which the heteropolymer will be polymerized.

It has been found experimentally that if a catalyst having a half-life of up to 6 hours at the temperature of polymerization is employed, about 0.2 gm to 2 gm is required per 100 g of total monomer to complete the reaction in a reasonable period of time, e.g. 4 to 6 hours. If a catalyst having a longer half-life is utilized, the time to complete the reaction is correspondingly longer. For example, isopropylperoxydicarbonate, a useful catalyst in this invention has a half-life of approximately 3 hours at 55°C. so that by maintaining polymerization temperatures at 55°C., a crosslinked heteropolymer is obtained after 4 to 6 hours. Benzoyl peroxide has a half-life of 100 hours at 55°C. but has a half-life of about 4 hours at 78°C. Heterpolymerization utilizing this catalyst should be conducted at about 78°C.

Among the catalysts useful in this invention are isopropylperoxydicarbonate, dichlorobenzoyl peroxide, azobisisobutyronitrile and benzoyl peroxide. All these catalysts have half-lives of 6 hours or less between 25°C. and 100°C. and are preferred in this invention. However, many other polymerization catalysts well known to those skilled in the art may also be applied if used at proper concentrations in the monomer solution as discussed above. In order to prepare the crosslinked heteropolymers of the instant invention the maleic derivative monomer, crosslinking agent, and catalyst solution must be added in controlled amounts to the vinyl ester solution where the reactants are polymerized to form the heteropolymer. The maleic derivative monomer and crosslinking agent must be added to the vinyl ester monomer solution so that the amounts of unreacted maleic derivative monomer and crosslinking agent in the vinyl ester reaction solution do not exceed 1/15th of the total amounts to be added.

Furthermore, the amount of catalyst added to the vinyl ester reaction solution must be added in amounts sufficient to heteropolymerize the reactants but in insufficient amount to cause formation of homopolyvinyl ester.

These controlled additions can be accomplished in several manners. One such method, which is the preferred manner, is to add the maleic derivative and crosslinking agent monomer solution in increments wherein each increment is less than 1/15th of the total amounts to be added. After each incremental addition of maleic derivative monomer and crosslinking agent an increment of the catalyst solution is added. The incremental catalyst addition is in such an amount that the catalyst polymerizes the maleic derivative monomer and the crosslinking agent monomer with vinyl ester monomer, but the amount is insufficient to promote homopolymerization of the vinyl ester. The correct addition of catalyst can be accomplished by adding an increment of catalyst solution wherein the ratio of the catalyst increment to the total amount of catalyst to be added is equivalent to the ratio of the incremental additions of maleic derivative and crosslinking agent to the total amounts of maleic derivative and crosslinking agent to be added. Sufficient time is allowed after each catalyst incremental addition for all the maleic derivative monomer and crosslinking agent in the vinyl ester reaction solution to form crosslinked heteropolymer. Generally, the incremental amount of monomers is consumed in about 10 minutes. These incremental additions are continued and followed with sufficient reaction times until all the maleic derivative monomer and crosslinking agent has been added to the vinyl ester monomer solution and all the crosslinked heteropolymer is formed. During the incremental additions and subsequent reaction periods, the vinyl ester solution is maintained at a suitable polymerizable temperature as described above. As the crosslinked heteropolymer is formed it precipitates out of the solution while the unreacted monomers remain in solution. After all the crosslinked heteropolymer is formed the crosslinked heteropolymer is recovered by a suitable separation technique such as filtering.

As a variation of this method the catalyst solution can be combined with the maleic derivative monomer crosslinking agent monomer solution and added concurrently to the vinyl ester reaction solution. This can be accomplished by selecting a catalyst which has a sufficiently high half-life at ambient temperature so as not to promote premature reaction of the maleic derivative-crosslinking agent solution but also has a sufficiently low half-life at an elevated reaction temperature so that heteropolymerization of the vinyl ester-maleic derivative-crosslinking agent occurs.

The controlled additions of the maleic derivative-crosslinking agent solution and the catalyst solution can also be accomplished by continuous additions. The continuous additions can be either dropwise of trickle flow. As the maleic derivative-crosslinking agent solution is added to the vinyl ester reaction solution, the amounts of the maleic derivative monomer and crosslinking agent begin to increase. As the crosslinked heteropolymer is formed, however, the maleic derivative monomer and crosslinking agent is consumed and this tends to decrease the amounts of maleic derivative monomer and crosslinking agent in the reaction solution. The rate of addition of the maleic derivative monomer-crosslinking agent solution in relation to the rate of formation of the crosslinked heteropolymer must be such that the amounts of maleic derivative and crosslinking agent monomer in the reaction solution do not exceed 1/15th of the total amounts of these monomers to be added.

Similarly the continuous rate of addition of the catalyst must be such that sufficient catalyst is available to promote heteropolymerization but in insufficient amounts to promote homopolymerization of the vinyl ester.

The vinyl ester reaction solution is maintained at a suitable polymerization temperature during the additions and the additions and reactions are continued until all the crosslinked heteropolymer is formed. The crosslinked heteropolymer is then separated from the solution as described above.

It has been found that when crosslinked heteropolymers are prepared by methods other than the above described controlled addlitions of maleic derivative monomer, crosslinking agent and catalyst solutions to the vinyl ester reactions solution, the crosslinked heteropolymers do not exhibit the superior properties of the crosslinked heteropolymers of the instant invention.

The crosslinked heteropolymers of this invention can be used directly after recovery as aqueous thickeners. The crosslinked heteropolymers efficiently thicken such systems as cosmetics, latex paints and other aqueous formulations. Many of the crosslinked heteropolymers form clear gels which are particularly useful in cosmetic formulations where clarity and hence aesthetic appeal to the user is desirable. Non-clear gels containing the instant crosslinked heteropolymer are useful in such products as paints, toothpastes and other household products.

In another embodiment of this invention, derivatives of the combined maleic anhydride portion of the crosslinked heteropolymers are provided which have special utility. These can be described by reference to the following reaction sequence.

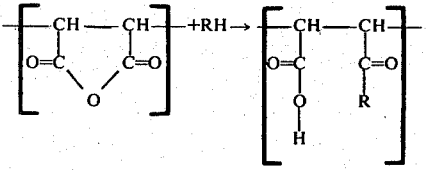

Combined maleic anhydride portion.

FORMULA 1

By reacting the combined maleic anhydride portion with compound RH wherein H is hydrogen and R is a radical selected from the group consisting of hydroxyl, alcoholate, substituted alcoholate, glycolate, amino and substituted amino, derivatives of the heteropolymer are produced. The half-ester of the maleic anhydride portion wherein R is an alcoholate radical and the half-amide, wherein R is an amino radical have special utilities in this invention. The half-ester is an excellent thickener for alcoholic systems. For example, the methyl ester (R=OCH$_3$) is an excellent gellant for methanol and ethanol. The glycolate ester (R=OCH$_2$C-H$_2$OH) is an excellent gellant for ethylene glycol. The half-amide is useful as a water-treatment additive to remove particulate matter such as sodium lignosulfonate, inorganic phosphates and other materials which are found for example in waste water or sewage. When R is hydroxyl, the maleic portion is maleic acid. This acid form as well as ammonium or alkaline earth metal salts thereof are also useful aqueous thickeners.

In order to more fully describe the instant invention the following examples are given.

EXAMPLE 1

This example illustrates the preparation of vinyl acetate and maleic anhydride heteropolymer crosslinked with allyl methacrylate.

To a 375 liter reactor was charged with 36.1 kg (420 m) of vinyl acetate and 50 kg. of thiophene free benzene. The reactor was equipped with a gas sparger, two calibrated containers for monomer and catalyst additions, a stirrer and a condenser which was vented to the atmosphere. The reactor was swept with nitrogen and then the nitrogen was diverted to the top of the condenser.

In a separate container, 17.6 kg (180 m) of maleic anhydride was dissolved in 119.2 kg of benzene with agitation. After dissolution of the maleic anhydride, the solution was sparged with nitrogen for 1 hour, and then 540 g of allyl methacrylate was added to the solution. The mole ratio of vinyl acetate monomer to maleic anyhdride monomer was 2.33 and the weight percent of the allyl methacrylate crosslinking agent based on the total amount of vinyl acetate, maleic anhydride, and allyl methacrylate monomers was 0.99 percent.

To another container was charged 22 kg of benezene which was sparged with nitrogen for 1 hour. Then 140 g of benzoyl peroxide catalyst was dissolved in the benzene.

The maleic solution was pumped into the calibrated container which was placed above the reactor so that gravity additions could be made. Similarly, the catalyst solution was transferred to a calibrated container above the reactor. These solutions were sparged with nitrogen while waiting for addition to the reactor.

Next the reactor contents were heated to 78°C. with constant agitation. Then 6 liters of the maleic derivative solution (1/25th of the total) and 1 liter of catalyst solution (1/25th of the total) were added to the reactor. After 10 minutes similar additions were again made. These additions, followed by 10 minute intervals, were continued until all the maleic anhydride monomer, crosslinking agent monomer, and catalyst were added to the reactor. After the last addition, temperature and agitation were maintained for 50 minutes. The reaction was terminated by sparging the solution with air and cooling to 40°C. The reaction mixture was then filtered in a bag centrifuge and dried in vacuum at 40°C. to constant weight. A yield of 34 kg (63 percent) of product was obtained. The product was analyzed and found to contain a vinyl acetate to maleic anhydride mole ratio of 1.33:1.

The product was added to water under shear to form an 0.5 weight percent polymer in water solution. The formed solution was found to be very clear and viscous and suitable for such uses as cosmetics. The initial equilibrium viscosity of this 0.5 percent aqueous solution when measured by a Brookfield viscometer Model RTV at 25°C. and 100 RPM was 20,000 cps. The 0.5 percent aqueous solution was then heated and maintained at an elevated temperature of 40.5°C. in order to measure viscosity stability under accelerated conditions. After 30 days, the viscosity decreased and stabilized. The stabilized viscosity measured at 25°C and as described above, was found to be 14,000 cps. The results are recorded in Table 1.

EXAMPLE 2

This example is presented as a control wherein a similar crosslinked heteropolymer as in Example 1 is prepared except all the reactants and catalyst were initially added to the reaction vessels and the controlled additions of maleic anhydride, crosslinking agent and catalyst described in Example 1 were not employed.

In this example the ratio of reactants and catalyst were the same as Example 1, however, smaller proportions of each were employed to afford better control of the exotherm.

To a 500 ml reaction flask was charged 15.05 g (0.175 m) of vinyl acetate, 7.35 g (0.075 m) of maleic anhydride, 0.225 g of allyl methacrylate, 0.058 g of benzoyl peroxide, and 87.5 ml of benzene. While under a nitrogen blanket and constant agitation, the contents in the reaction flask were heated to 75°C. The contents were maintained at this temperature for 290 minutes to allow the crosslinked heteropolymer to form. The reaction mixture was then cooled to terminate the reaction and agitation was stopped. Next the reaction mixture was filtered and washed with benzene to recover a product. Yield of the product was about 65 percent and product was found to contain a vinyl acetate to maleic anhydride ratio of 1.24:1.

A 0.5 weight percent polymer in water solution was prepared and the initial equilibrium viscosity and stabilized viscosity was determined as in Example 1. The initial equilibrium viscosity of this solution was found to be 17,000 cps as compared to 20,000 cps of Example 1. After 30 days at an elevated temperature of 40.5°C. the viscosity of this solution leveled off at about 10,500 cps as compared to the stabilized viscosity of 14,000 cps of Example 1. The results are recorded in Table 1.

EXAMPLE 3

This example is presented as a control wherein a similar crosslinked heteropolymer as in Example 1 is prepared except only the catalyst is added under controlled additions and the other reactants are initially charged to the reaction flask.

In this example the ratio of reactants and catalyst were the same as Example 1, however, smaller proportions of each were employed.

To a 500 ml reaction flask was charged 60.2 g. (0.7 m) of vinyl acetate, 29.4 gms (.3 m) of maleic anhydride, 0.9 gms of allyl methacrylate and 300 ml of thiophene free benzene. The reaction flask was equipped with an agitator, thermometer, reflux condenser, nitrogen inlet, and an addition funnel. The addition funnel contained 0.233 gms of benzoyl peroxide in 50 ml of benzene. The reaction solution in the reaction flask was heated to 75°C. and while under agitation and under a blanket of nitrogen, 2 ml (1/25th of the total) of the catalyst solution was added to the reaction flask. After 10 minutes another 2 ml of catalyst solution was added. The catalyst solution additions at 10 minute intervals were continued until all the catalyst solution was added. After the last catalyst addition, the reaction was continued for an additional 50 minutes. The formed crosslinked heteropolymer was then filtered and washed with benzene to obtain a product. The product has a yield of 63 percent, and the mole ration of vinyl acetate to maleic anhydride benzene was found to be 1.18:1.

As in Example 1 a 0.5 weight percent polymer in water solution was prepared and viscosity determinations made. The initial equilibrium viscosity was found to be 17,000 cps as compared to 20,000 cps of Example 1, and the stabilized viscosity was found to be 5,500 cps as compared to 14,000 cps of Example 1. The results are recorded in Table 1.

EXAMPLE 4

This example is also presented as a control wherein a similar crosslinked heteropolymer as in Example 1 is prepared except only the catalyst and crosslinking agent are added under controlled additions and the other reactants are initially charged to the reaction flask as opposed to Example 1 where the catalyst, crosslinking agent, and maleic anhydride are added under controlled additions.

In the example the ratio of reactants and catalyst were the same as Example 1 except smaller proportions were employed.

To a 500 ml reaction flask was charged 60.2 g (0.7 m) of vinyl acetate, 29.4 g. (0.3 m) maleic anhydride and 250 ml of thiophene free benzene. The reaction flask was equipped with an agitator, thermometer, reflux condensor, nitrogen inlet, and addition funnels. One addition funnel contained 0.9 gms of crosslinking agent in 50 ml of benzene and the other addition funnel contained 0.233 gms of benzoyl peroxide in 50 ml of benzene. The reaction solution in the reaction flask was heated to 75°C. and while under agitation and under a blanket of nitrogen, 2 ml (1/25th of the total) of the crosslinking agent solution was added to the reaction flask. This addition was followed by a 2 ml addition (1/25th of the total) of the benzoyl peroxide solution. After 10 minutes another 2 ml of crosslinking agent solution was added followed by another 2 ml addition of benzoyl peroxide. The additions were continued until all the crosslinking agent and benzoyl peroxide were added. The formed heteropolymer was then filtered and washed as described in Example 1.

The product had a yield of 64 percent, and the mole ratio of the vinyl acetate to the maleic derivative was found to be 1.13:1.

A 0.5 weight percent polymer in water solution was prepared and the initial equilibrium viscosity and viscosity stability was determined as in Example 1. The initial equilibrium viscosity of this solution was found to 12,500 cps as compared to 20,000 cps of Example 1 and the stabilized viscosity was found to be 2,000 cps as compared to 14,000 of Example 1. The results are recorded in Table I.

Control Examples 2, 3, and 4 clearly show that the controlled additions of maleic derivative, crosslinking agent, and catalysts as described in this instant invention produces a superior product, than products formed where these controlled additions are not employed.

TABLE I

| Example | Additions | Initial Viscosity* (cps) | Stabilized Viscosity* (cps) |
|---|---|---|---|
| 1 | Controlled additions of maleic anhydride, crosslinking agent and catalyst | 20,000 | 14.000 |
| 2 (Control) | No controlled additions. All reactants initially in reaction flask | 17,000 | 10,500 |
| 3 (Control) | Controlled addition of catalyst only. | 17,000 | 5,500 |
| 4 (Control) | Controlled addition of catalyst and crosslinking agent only. | 12,500 | 2,000 |

*Viscosity of 0.5 weight % polymer in aqueous solution measured by Brookfield Viscometer Model RTV at 100 RPM and 25°C. after neutralization with triethanol amine to a pH of 7.

EXAMPLE 5

This example illustrates the preparation of a crosslinked heteropolymer of vinyl acetate and maleic anhydride crosslinked with allyl methacrylate wherein toluene rather than benzene was used as the solvent.

To a 1000 ml flask was added 60.2 g (0.7 mole) of vinyl acetate and 70 ml of toluene. The flask was equipped with a stirrer, a nitrogen inlet, a 250 ml dropping funnel, a 50 ml dropping funnel and a condenser. A maleic anhydride - crosslinking agent solution was prepared by dissolving 29.4 g (0.3 m) of maleic anhydride and 1.4 g of allyl methacrylate in toluene to a total volume of 250 ml. The catalyst solution was prepared by dissolving 0.25 g of benzoxl peroxide in 52 ml of toluene. With nitrogen purging and constant agitation, the contents of the flask were heated to 75°C and maintained at this temperature throughout the reaction. Next, 10 ml of the maleic anhydride-crosslinking agent solution was added and followed by a 4 ml addition of catalyst solution. After 10 minutes another 10 ml of maleic anhydride-crosslinking agent solution was added and followed by a 2 ml addition of catalyst solution. These additions, at 10 minuted intervals were continued until all the maleic anhydride, crosslinking agent and catalyst were added. Approximately 50 minutes after the last addition the reaction mixture was guenched with air, cooled, filtered, and dried to give 58.4 g of product.

A 0.5 percent polymer in water solution had a Brookfield viscosity of 5940 cps at 100 rpm.

EXAMPLE 6

This example illustrates the utility of the instant crosslinked heteropolymer prepared in a toluene solvent as a clear gellant for cosmetic formulations.

A skin care lotion was prepared by first adding the following ingredients to a 250 ml Erlenmeyer flask:
3 g propylene glycol
0.2 g methyl paroben (preservative)
68.5 g water The above mixture was heated to 70°C and 0.6 g of the crosslinked heteropolymer of Example 5 was added with stirring to the mixture. After the polymer dissolved, the mixture was cooled and transferred to a small Waring blender.

To the above was then added to a premix of:
20 g ethanol
2.0 g Cetral HE (Henkel Co.)
0.3 perfume and a premix of
5 g water and
2.5 g triisoproparolamine The resulting formulation was a thick, clear lotion which possessed a smooth feel when rubbed on the skin. After drying there was no tacky feel to the skin.

The Brookfield viscosity of this solution was 5940 cps at 100 rpm.

EXAMPLE 7

This example illustrates the preparation of several heteropolymers of vinyl acetate and maleic anhydride crosslinked with various amounts of allyl methacrylate crosslinking agent.

Exactly 60.2 g (0.7m) of vinyl acetate in 70 ml of thiophene-free benzene was charged to a 500 ml reaction flask equipped with a stirrer, therometer, reflux condenser, nitrogen inlet tube and two addition funnels. The first addition funnel contained a solution of maleic anhydride, 29.4 g (0.3 m), and 1.5 g of allyl methacrylate in 250 ml of benzene. The second contained 0.045 g of isopropyl peroxydicarbonate in 50 ml of benzene. The vinyl acetate solution was heated to 55°C and while under a blanket of nitrogen, 10 ml of maleic anhydride-crosslinking agent solution (1/25 of the total) was added to the vinyl acetate solution. This was immediately followed by 2 ml of the catalyst solution. After 10 minutes the above additions of maleic anhydride-crosslinking agent solution and catalyst solution were repeated followed by a 10 minute interval between additions until all solutions were added and 10 minutes had elapsed. The reaction mixture was then filtered to recover a crude product. The filter cake was washed with benzene to remove any unreacted vinyl acetate. Yield of product based on total weight of monomers was about 64%.

The product was analyzed for maleic anhydride content and was found to contain 42.4 mole percent of maleic anhydride and 57.6 mole percent of vinyl acetate. The Brookfield viscosity of the polymer as a 1% solution in water at 25°C was 24,800 cps at 100 rpm.

Several other heteropolymers were prepared employing the above procedure wherein the amounts of allyl methacrylate were varied. The amounts used were 0.5g, 0.8gg and 0.9g. These heteropolymers including the heteropolymer prepared above were tested for viscosity stability by determining the Brookfield viscosity of 1 percent aqueous gels prepared with samples of these heteropolymers after 5, 8, 9, 13 and 14 days.

These results are shown in Table 2. All Brookfield viscosities were determined at 100 rpm at 25°C.

TABLE 2

| TIME | WEIGHT OF ALLYL METHACRYLATE (g) | | | |
|---|---|---|---|---|
| | 0.5 | 0.8 | 0.9 | 1.5 |
| 5 days | | 14,800 cps | 14,000 cps | |
| 8 days | 7000 cps | | | 26,200 cps |
| 9 days | | 13,800 cps | 13,240 cps | |
| 13 days | | 13,320 cps | 12,640 cps | |
| 14 days | 7200 cps | | | 25,000 cps |

As the table shows, the heteropolymers prepared impart high viscosities to water and maintained viscosity stability.

In another series of experiments, the above heteropolymers were evaluated for clarity and viscosity as for example for use in cosmetics by neutralizing a 1 percent solution of the heteropolymer with an organic amine.

A 1 percent solution of the heteropolymer was stirred in water at 70°C for 30 minutes in an Erlenmeyer Flask with a magnetic stirrer. The solution was then transferred to a Waring Blender and while stirring at medium speed was neutralized with triethanol amine (TEA) until the pH was just above 7. The procedure was then repeated using triisopropanol amine (TIPA). The neutralization procedure was then carried out for each heteropolymer.

The resulting neutralized heteropolymer solutions were then examined for appearance, clarity and viscosity. Table 3 summarizes the results.

TABLE 3

| Weight Allyl Methacrylate (g)* | Amine | g. Amine/g. Heteropolymer | Appearance | Viscosity |
|---|---|---|---|---|
| 0.5 | TEA | 1.0 | Clear | 14,280 |
| 0.5 | TIPA | 1.5 | Clear | 14,680 |
| 0.8 | TEA | 1.0 | Slightly Cloudy | 20,000 |
| 0.8 | TIPA | 1.5 | Slightly Cloudy | 21,440 |
| 0.9 | TEA | 1.0 | Cloudy | 29,320 |
| 0.9 | TIPA | 2.0 | Cloudy | 33,200 |
| 1.5 | TEA | 1.0 | Turbid | ¹not measured |
| 1.5 | TIPA | 1.0 | Turbid | ¹not measured |

¹Indicates that gels formed too thick to accurately measure.
*Based on 89.6 g. monomer charge.

As Table 3 shows, clear gels are obtained using heteropolymers of this invention with low amounts of crosslinking agent e.g. from 0.5 g to 0.8 g. As the amount of crosslinking agent increases, the gels become cloudy but more viscous making them more suitable for example as non-clear gellants in, for example, pigmented aqueous-based compositions such as paints or toothpastes.

EXAMPLES 8–15

This example illustrates the preparation of several vinyl acetate-maleic anhydride heteropolymers crosslinked with different amounts and types of crosslinking agents.

Following the procedure of Example 7, and using the same quantities of materials described therein, a series of heteropolymers were prepared except employing crosslinking agents different from the allyl methacrylate of Example 7, and different quantities thereof. Brookfield viscosities were determined in all experiments.

Table 4 summarizes the results.

TABLE 4

| Example | Type of Crosslinking Agent | Amount of Crosslinking Agent (g) | Mole Ratio of Combined Vinyl Acetate to Maleic Anhydride | Brookfield Viscosity (at 100 RPM) |
|---|---|---|---|---|
| 2 | Allyl Acrylate | 0.7 | 1.34 | 18,200 cps at 0.5% |
| 3 | Diallyl Maleate | 3.0 | 1.53 | 19,840 cps at 1.0% |
| 4 | Trimethylolpropane Trimethacrylate | 3.0 | 1.50 | 14,240 cps at 1.0% |
| 5 | Triallylisocyanurate | 2.0 | 1.30 | 14,480 cps at 1% |
| 6 | Triallyl Phosphate | 3.0 | 1.20 | 1,136 cps at 1% |
| 7 | Divinyl Benzene | 1.5 | 1.50 | 1,028 cps at 1% |
| 8 | Triallyl Cyanurate | 2.0 | 1.10 | 57 cps at 1% |
| 9 | Ethylenedimethacrylate | 2.0 | 2.1 | 13,760 cps at 2% |

EXAMPLE 16

This example illustrates the preparation of the methyl ester of a crosslinked vinyl acetate-maleic anhydride heteropolymer.

Exactly 30 g of the crosslinked heteropolymer of Example 1 but containing 0.5 g of diallyl phthalate instead of allyl methacrylate crosslinking agent was placed in 500 ml of methanol in a round-bottomed flask. The mixture was heated to reflux and 0.09 g. of concentrated HCl was added as an esterification catalyst. The polymer dissolved as it reacted to form the ester.

The product had an acid number of 280. The starting heteropolymer had an acid number of 539 which indicated formation of a half-ester.

The esterified heteropolymer was able to thicken methanol solvent to point that stirring became extremely difficult. In a similar experiment, ethylene glycol was substituted for the methanol above to produce a glycolate half-ester which thickened the glycol reaction medium as it reacted.

EXAMPLE 17

This example illustrates the utility of the instant crosslinked heteropolymer prepared using benzene as a solvent as a clear gellant for cosmetic formulations.

A skin care lotion was prepared by first adding the following ingredients to a 250 ml Erlenmeyer flask:
3 g propylene glycol
0.2 g methyl paraben (preservative)
68.5 g water The above mixture was heated to 70°C. and 0.5 g of the crosslinked heteropolymer of Example 7 containing 0.5 percent allyl acrylate was added with stirring to the mixture. After the polymer dissolved, the mixture was cooled and transferred to a small Waring blender.

To the above was then added a premix of:
20 g ethanol
2.0 g Cetral HE (Henkel Co.)
0.3 g perfume
and a premix of
5 g water and
2.5 g triisopropanolamine The resulting formulation was a thick, clear lotion which possessed a smooth feel when rubbed on the skin. After drying there was no tacky feel to the skin.

EXAMPLE 18

This example illustrates the preparation of an amide derivative of crosslinked heteropolymer.

Exactly 1204 g (14 m) of vinyl acetate in 1650 ml of thiophene free benzene was charged to a 12 l. reaction flask equipped with stirrer, thermometer, reflux condenser, nitrogen inlet tube and two addition funnels. The first funnel contained a solution of 588 g (6 m) of maleic anhydride and 35.84 g of diallyl phthalate in 4500 ml of thiophene-free benzene. The second funnel contained 0.914 g of isopropylperoxydicarbonate in 250 ml of benzene. The vinyl acetate solution was heated to 55°C. and while under a blanket of nitrogen, 180 ml of the maleic anhydride - crosslinking agent solution (1/25 of total) was added to the vinyl acetate solution. This was immediately followed by 10 ml of the catalyst solution. After 10 minutes the above additions of maleic anhydride-diene solution and caralyst solutions were repeated until all solutions were added and 10 minutes had elapsed. After filtering to recover the heteropolymer it was found by analysis that the product contained 44.2 mole percent combined maleic anhydride and had a Brookfield viscosity of 1776 cps at 100 rpm (2% solids in water).

Exactly 500 g of the above heteropolymer was placed in a 12 liter flask and 4 liters of benzene was added. Ammonia gas ($NH_3$) was bubbled into the mixture at a rate rapid enough to exclude air during cooling. The addition of ammonia was continued until the temperature of the mixture reached room temperature. After the presence of ammonia was detected at the outlet of the flask as evidenced by wet litmus paper, the mixture was again heated to 60°C. to remove excess ammonia.

The mixture was filtered and washed with benzene and had an acid number of 253 compared to a theoretical acid number of 251.

The amide was used in an aqueous medium to test its ability to remove particulate matter such as sodium ligno-sulfonate and sodium orthophosphate according to the following procedures;

A ALUM TREATED WATER CONTAINING LIGNOSULFONATE

Blank water was prepared by adding 334 ppm of sodium lignosulfonate to tap water and coagulating it with 400 ppm of alum. After stirring for 15 seconds at 100 rpm using a high speed stirrer, 10 ppm of the amide derivative of the crosslinked heteropolymer was added and stirred 15 seconds at 100 rpm, 15 seconds at 40 rpm, and one minute at 20 rpm. Size of floc, supernatant appearance and sludge volume were observed. The turbidity of the supernatant was measured after 1 minute, 3 minutes and 5 minutes using a Hach meter. Turbidities were reported in Jackson Turbidity Units.

| Turbidity (JTU) | |
| --- | --- |
| 1 minute | 255 |
| 3 minutes | 50 |
| 5 minutes | 43 |

B-ALUM TREATED WATER CONTAINING ORTHOPHOSPHATE

Blank water was prepared by adding 500 ppm disodium phosphate to tap water and coagulating it with 1,000 ppm of alum. Following the procedure described above for the Alum Treated Water Containing Lignosulfonate, 5 ppm of the amide derivative was added. Turbidity was measured after 1 minute and 3 minutes and is listed below.

| Turbidity (JTU) | |
| --- | --- |
| 1 minute | 95 |
| 3 minutes | 35 |

The above turbidity data for A and B above indicate the amide derivative prepared above is an excellent water-treatment additive for the removal of particulate matter.

EXAMPLE 19

In this example, a heteropolymer containing 43.2 mole percent combined maleic anhydride crosslinked with 0.9 g of allyl methacrylate was tested for its thickening properties in water at 1 percent by weight and compared to other aqueous thickeners known in the art. Table 5 below summarizes the results of Brookfield viscosity measurements from 0.5 to 100 rpm for each thickener tested.

TABLE 5

| | RPM | | | | | | | |
| --- | --- | --- | --- | --- | --- | --- | --- | --- |
| | .5 | 1.0 | 2.5 | 5 | 10 | 20 | 50 | 100 |
| Crosslinked Vinyl Acetate-Maleic Anhydride | 1,440,000 | 788,000 | 392,000 | 326,000 | 148,000 | 91,000 | 48,000 | 28,000 |
| QP 100 M (Union Carbide) | 7,200 | 6,800 | 6,080 | 5,360 | 4,480 | 3.580 | 2,432 | 1,708 |
| Methocel 90 HG (Dow Chemical Co.) | 800 | 700 | 680 | 680 | 650 | 615 | 542 | 469 |

TABLE 5-continued

| | .5 | 1.0 | 2.5 | RPM 5 | 10 | 20 | 50 | 100 |
|---|---|---|---|---|---|---|---|---|
| CMC 4H1 (Hercules) | 4,400 | 3,400 | 2,040 | 1,460 | 1,070 | 845 | 610 | 477 |
| Natrasol 250 HR (Hercules) | 2,400 | 2,400 | 2,160 | 2,040 | 1,800 | 1,500 | 1,124 | 840 |
| Guar Gum Type M (Meer Corp.) | 9,200 | 8,600 | 6,960 | 5,600 | 4,240 | 3,000 | 1,780 | 1,158 |
| Viscarine (Marine Colloids Inc.) | 800 | 700 | 680 | 660 | 610 | 550 | 450 | 366 |
| Keltex P (Kelco Co.) | 400 | 300 | 320 | 320 | 320 | 305 | 286 | 263 |
| Kelzan (Kelco Co.) | 38,600 | 19,500 | 9,640 | 5,760 | 3,150 | 1,860 | 880 | 501 |

We claim:

1. A process for preparing crosslinked heteropolymers of vinyl ester and maleic derivatives by combining vinyl ester monomers, maleic derivative monomers, and crosslinking agent monomers, wherein the mole ratio of vinyl ester monomers to maleic derivative monomers is from 1.1:1 to 3:1 and wherein the amount of crosslinking agent monomers is from 0.2 to 3 weight percent based on the total amount of monomers which comprises the steps of:
   a. providing a vinyl ester monomer solution wherein the vinyl ester monomer solution is the reaction solution;
   b. providing a maleic derivation monomer-crosslinking agent monomer solution;
   c. providing a catalyst solution;
   d. adding an amount of the maleic derivative monomer-crosslinking agent monomer solution to the reaction solution to form a polymerizable solution wherein the added amount is such that the unreacted amounts of the maleic derivative monomer and cross-linking agent monomer in the reaction solution do not exceed 1/15th of the total amounts to be added.
   e. adding an amount of catalyst solution wherein the added amount is sufficient to promote heteropolymerization but in an insufficient amount to promote homopolymerization of the vinyl ester;
   f. polymerizing the reaction solution at a polymerizable temperature; and
   g. repeating steps (d), (e), and (f) until all the maleic derivative monomers, crosslinking agent monomers, and catalyst has been added and the heteropolymer formed wherein the mole ratio of the combined vinyl ester to combined maleic derivatives in the heteropolymer is from 1.1:1 to 3:1.

2. The process according to claim 1 wherein the mole ratio of vinyl ester monomers to maleic derivative monomers is from 1.2:1 to 1.5:1.

3. The process according to claim 1 wherein the amount of crosslinking agent monomers is from 0.5 to 2.0 weight percent based on the total amount of monomers.

4. The process according to claim 1 wherein the vinyl ester is vinyl acetate.

5. The process according to claim 1 wherein the cross-linking agent is allyl methacrylate.

6. The process according to claim 1 wherein the maleic derivative is selected from the group consisting of maleic anhydride, maleic acid, maleic acid salts, esters of maleic acid and amides of maleic acid.

7. The process according to claim 6 wherein the maleic derivative is maleic anhydride.

8. The process according to claim 1 wherein the maleic derivative is represented by the formula:

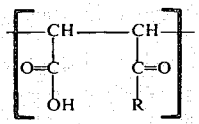

wherein R is a radical selected from the group consisting of hydroxyl, alcoholate, substituted alcoholate, glycolate, amino and substituted amino.

9. The process according to claim 1 wherein the catalyst is selected from the group consisting of isopropyl peroxydicarbonate, dichlorobenzoyl peroxide, benzoyl peroxide and azobisisobutyronitrile.

10. The process according to claim 9 wherein the catalyst is benzoyl peroxide.

11. A crosslinked heteropolymers of vinyl ester and maleic derivatives prepared by the process of combining vinyl ester monomers, maleic derivative monomers, and crosslinking agent monomers, wherein the mole ratio of vinyl ester monomers to maleic derivative monomers is from 1.1:1 to 3:1 and wherein the amount of crosslinking agent monomers is from 0.2 to 3 weight percent based on the total amount of monomers which comprises the steps of:
   a. providing a vinyl ester monomer solution wherein the vinyl ester monomer solution is the reaction solution;
   b. providing a maleic derivative monomer-crosslinking agent monomer solution;
   c. providing a catalyst solution;
   d. adding an amount of the maleic derivative monomer-crosslinking agent monomer solution to the reaction solution to form a polymerizable solution wherein the added amount is such that the unreacted amounts of the maleic derivative monomer and crosslinking agent monomer in the reaction solution do not exceed 1/15th of the total amounts to be added;
   e. adding an amount of catalyst solution wherein the added amount is sufficient to promote heteropolymerization but in an insufficient amount of promote homopolymerization of the vinyl ester;
   f. polymerizing the reaction solution at a polymerizable temperature; and
   g. repeating steps (d), (e), and (f) until all the maleic derivative monomers, crosslinking agent monomers, and catalyst has been added and the heteropolymer formed wherein the mole ratio of the combined vinyl ester to combined maleic derivatives in the heteropolymer is form 1.1:1 to 3:1.

* * * * *